US011721429B1

(12) United States Patent
Mayer et al.

(10) Patent No.: US 11,721,429 B1
(45) Date of Patent: Aug. 8, 2023

(54) EVENT PREDICTION BASED ON MEDICAL SERVICE AND PROVIDER INFORMATION USING AN ARTIFICIAL INTELLIGENCE PREDICTION ENGINE

(71) Applicant: Change Healthcare Holdings LLC, Nashville, TN (US)

(72) Inventors: Christopher Mayer, Johns Creek, GA (US); Balaji Lakshmi Ramakrishnan, Alpharetta, GA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 195 days.

(21) Appl. No.: 17/038,667

(22) Filed: Sep. 30, 2020

(51) Int. Cl.
*G16H 40/20* (2018.01)
*G16H 50/70* (2018.01)
*G06Q 40/08* (2012.01)
*G06N 20/00* (2019.01)
*G06Q 10/10* (2023.01)
*G16H 70/20* (2018.01)
*G06Q 40/12* (2023.01)

(52) U.S. Cl.
CPC ............ *G16H 40/20* (2018.01); *G06N 20/00* (2019.01); *G06Q 10/10* (2013.01); *G06Q 40/08* (2013.01); *G06Q 40/12* (2013.12); *G16H 50/70* (2018.01); *G16H 70/20* (2018.01)

(58) Field of Classification Search
CPC ........ G16H 50/70; G16H 20/10; G16H 20/00; G16H 50/30; G06Q 40/08; G06Q 30/0202
See application file for complete search history.

(56) References Cited

U.S. PATENT DOCUMENTS

| 2013/0054259 A1* | 2/2013 | Wojtusiak | G06Q 10/10 705/2 |
| 2016/0078552 A1* | 3/2016 | Mercer | G06Q 10/10 705/2 |
| 2020/0152332 A1* | 5/2020 | Yang | G16H 50/20 |
| 2020/0258630 A1* | 8/2020 | Ivanoff | G06Q 10/10 |

FOREIGN PATENT DOCUMENTS

WO WO-2019022779 A1 * 1/2019 ......... F02M 51/0671

OTHER PUBLICATIONS

Desai, Rishi J., et al. "Comparison of machine learning methods with traditional models for use of administrative claims with electronic medical records to predict heart failure outcomes." JAMA network open 3.1 (2020): e1918962-e1918962. (Year: 2020).*

* cited by examiner

*Primary Examiner* — Linh Giang Le
*Assistant Examiner* — Constantine Siozopoulos
(74) *Attorney, Agent, or Firm* — Myers Bigel, P.A.

(57) ABSTRACT

A method includes receiving information associated with a stimulus, the information associated with the stimulus comprising first information associated with a medical claim for services provided to a patient and second information associated with a provider that provided the services to the patient; and predicting, using an artificial intelligence engine, when an event will occur in response to the stimulus.

13 Claims, 9 Drawing Sheets

EVENT PREDICTION BASED ON MEDICAL SERVICE AND PROVIDER INFORMATION USING AN ARTIFICIAL INTELLIGENCE PREDICTION ENGINE

FIELD

The present inventive concepts relate generally to health care systems and services and, more particularly, to the use of artificial intelligence systems that can be used by health care providers for event prediction.

BACKGROUND

Health care service providers have patients that pay for their care using a variety of different payors. For example, a medical facility or practice may serve patients that pay by way of different insurance companies including, but not limited to, private insurance plans, government insurance plans, such as Medicare, Medicaid, and state or federal public employee insurance plans, and/or hybrid insurance plans, such as those that are sold through the Affordable Care Act. Typically, health care providers estimate future payments/collections using a waterfall model in which a payment is estimated to arrive an estimated time after a claim is issued to a payor (e.g., insurer). These estimates, however, can be inaccurate as they often do not account for differences between payors and differences between types of services billed for. The volatility in payment patterns based on payor and services billed for may make managing a medical facility or practice more difficult.

SUMMARY

According to some embodiments of the inventive concept, a method comprises receiving information associated with a stimulus, the information associated with the stimulus comprising first information associated with a medical claim for services provided to a patient and second information associated with a provider that provided the services to the patient; and predicting, using an artificial intelligence engine, when an event will occur in response to the stimulus.

In other embodiments, the first information associated with the medical claim comprises an identifier for a payor, a billing code for an encounter, and/or a date at which the medical claim was submitted to the payor; and the second information associated with the provider comprises an identifier for the provider and/or a provider specialty.

In still other embodiments, the stimulus comprises a filing of the medical claim with the payor; and the event comprises payment of the medical claim by the payor.

In still other embodiments, the method further comprises generating, using a machine learning engine, the artificial intelligence engine.

In still other embodiments, generating the artificial intelligence engine comprises receiving training information associated with the stimulus, the training information associated with the stimulus comprising first training information associated with a plurality of medical claims for services provided to a plurality of patients, respectively, and second training information associated with a plurality of providers that provided the services to the plurality of patients; detecting patterns in the training information associated with the stimulus; and generating the artificial intelligence engine based on the patterns detected in the training information associated with the stimulus.

In still other embodiments, the first training information associated with the plurality of medical claims comprises a plurality of identifiers for a plurality of payors, respectively, a plurality of billing codes for a plurality of encounters, respectively, a plurality of dates at which the plurality of medical claims were submitted to the plurality of payors, identifications of first ones of the plurality of medical claims for which a first plurality of payments were received from first ones of the plurality of payors in full satisfaction of invoiced amounts on the first ones of the plurality of medical claims, a first plurality of dates at which the first plurality of payments were received from first ones of the plurality of payors, identifications of second ones of the plurality of medical claims for which a second plurality of payments were received from second ones of the plurality of payors in amounts less than invoiced amounts on the second ones of the plurality of medical claims, respectively, a second plurality of dates at which the second plurality of payments were received from the second ones of the plurality of payors, identifications of third ones of the plurality of medical claims for which payments were never received from third ones of the plurality of payors, and a plurality of deficiencies corresponding to differences between the amounts less than the invoiced amounts and the invoiced amounts; and the second training information associated with the plurality of providers comprises a plurality of identifiers for the plurality of providers, respectively, and/or a plurality of specialties for the plurality of providers, respectively.

In still other embodiments, the first training information further comprises a plurality of ages associated with the plurality of medical claims, the plurality of ages comprising a plurality of differences between the plurality of dates at which the plurality of medical claims were submitted to the plurality of payors and the first plurality of dates at which the first plurality of payments were received from the plurality of payors and the second plurality of dates at which the second plurality of payments were received from the plurality of payors.

In still other embodiments, the event comprises a plurality of events corresponding to payments of the plurality of medical claims by the plurality of payors, respectively. The method further comprises applying a first modeling technique to the first plurality of payments and the first ones of the plurality of payors to determine a first payor effect on the payments of the plurality of medical claims; applying a second modeling technique to the second plurality of payments and the second ones of the plurality of payors to determine a second payor effect on the payments of the plurality of medical claims; applying a third modeling technique to the third ones of the plurality of medical claims for which payments were never received and the third ones of the plurality of payors to determine a third payor effect on the payments of the plurality of medical claims; applying a fourth modeling technique to the payments of the plurality of medical claims and the plurality of billing codes to determine a billing code effect on the payments of the plurality of medical claims; and applying a fifth modeling technique to the payments of the plurality of medical claims and the plurality of dates at which the medical claims were submitted to the plurality of payors to determine a date submission effect on the payments of the plurality of medical claims.

In still other embodiments, generating the artificial intelligence engine further comprises generating the artificial intelligence engine based on the first payor effect, the second payor effect, the third payor effect, the billing code effect, and the date submission effect.

In still other embodiments, the first information is further associated with a plurality of medical claims for services provided to a plurality of patients and the second information is further associated with a plurality of providers that provided the services to the plurality of patients; the stimulus comprises filing of a plurality of medical claims with a plurality of payors; the event comprises a plurality of events corresponding to payments of the plurality of medical claims by the plurality of payors, respectively; and predicting when the event will occur in response to the stimulus comprises predicting, using the artificial intelligence engine, when the plurality of events will occur in response to the stimulus.

In still other embodiments, predicting when the plurality of events will occur comprises forecasting, in a plurality of time intervals, a plurality of invoiced amounts, respectively, of the plurality of medical claims; and forecasting, in the plurality of time intervals a plurality of amounts of the payments, respectively, of the plurality of medical claims.

In still other embodiments, the first information associated with the plurality of medical claims for services provided to the plurality of patients further comprises a plurality of identifiers for the plurality of payors, respectively, a plurality of billing codes for a plurality of encounters, respectively, and a plurality of dates at which the plurality of medical claims were submitted, respectively, to the plurality of payors. The method further comprises forecasting, in the plurality of time intervals, a plurality of amounts of the payments, respectively, of the plurality of medical claims for each of the plurality of identifiers of the plurality of payors based on the plurality of dates at which the plurality of medical claims were submitted, respectively, to the plurality of payors; forecasting, in the plurality of time intervals, a plurality of amounts of the payments, respectively, of the medical claims for each of the plurality of billing codes for the plurality of encounters based on the plurality of dates at which the plurality of medical claims were submitted, respectively, to the plurality of payors; determining, in the plurality of time intervals, a plurality of ideal amounts of the payments, respectively, of the plurality of medical claims for each of the plurality of identifiers of the plurality of payors based on the plurality of dates at which the plurality of medical claims were submitted, respectively, to the plurality of payors; and determining in the plurality of time intervals, a plurality of ideal amounts of the payments, respectively, of the medical claims for each of the plurality of billing codes for the plurality of encounters based on the plurality of dates at which the plurality of medical claims were submitted, respectively, to the plurality of payors.

In some embodiments of the inventive concept, a system comprises a processor and a memory coupled to the processor and comprising computer readable program code embodied in the memory that is executable by the processor to perform operations comprising: receiving information associated with a stimulus, the information associated with the stimulus comprising first information associated with a medical claim for services provided to a patient and second information associated with a provider that provided the services to the patient; and predicting, using an artificial intelligence engine, when an event will occur in response to the stimulus.

In further embodiments, the first information associated with the medical claim comprises an identifier for a payor, a billing code for an encounter, and/or a date at which the medical claim was submitted to the payor; and the second information associated with the provider comprises an identifier for the provider and/or a provider specialty.

In still further embodiments, the stimulus comprises a filing of the medical claim with the payor; and the event comprises payment of the medical claim by the payor. The operations further comprise generating, using a machine learning engine, the artificial intelligence engine.

In still further embodiments, generating the artificial intelligence engine comprises receiving training information associated with the stimulus, the training information associated with the stimulus comprising first training information associated with a plurality of medical claims for services provided to a plurality of patients, respectively, and second training information associated with a plurality of providers that provided the services to the plurality of patients; detecting patterns in the training information associated with the stimulus; and generating the artificial intelligence engine based on the patterns detected in the training information associated with the stimulus.

In some embodiments of the inventive concept, a computer program product comprises a non-transitory computer readable storage medium comprising computer readable program code embodied in the medium that is executable by a processor to perform operations comprising: receiving information associated with a stimulus, the information associated with the stimulus comprising first information associated with a medical claim for services provided to a patient and second information associated with a provider that provided the services to the patient; and predicting, using an artificial intelligence engine, when an event will occur in response to the stimulus.

In other embodiments, the first information associated with the medical claim comprises an identifier for a payor, a billing code for an encounter, and/or a date at which the medical claim was submitted to the payor; and the second information associated with the provider comprises an identifier for the provider and/or a provider specialty.

In still other embodiments, the stimulus comprises a filing of the medical claim with the payor; and the event comprises payment of the medical claim by the payor. The operations further comprising generating, using a machine learning engine, the artificial intelligence engine.

In still other embodiments, generating the artificial intelligence engine comprises receiving training information associated with the stimulus, the training information associated with the stimulus comprising first training information associated with a plurality of medical claims for services provided to a plurality of patients, respectively, and second training information associated with a plurality of providers that provided the services to the plurality of patients; detecting patterns in the training information associated with the stimulus; and generating the artificial intelligence engine based on the patterns detected in the training information associated with the stimulus.

It is noted that aspects described with respect to one embodiment may be incorporated in different embodiments although not specifically described relative thereto. That is, all embodiments and/or features of any embodiments can be combined in any way and/or combination. Moreover, other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter, and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
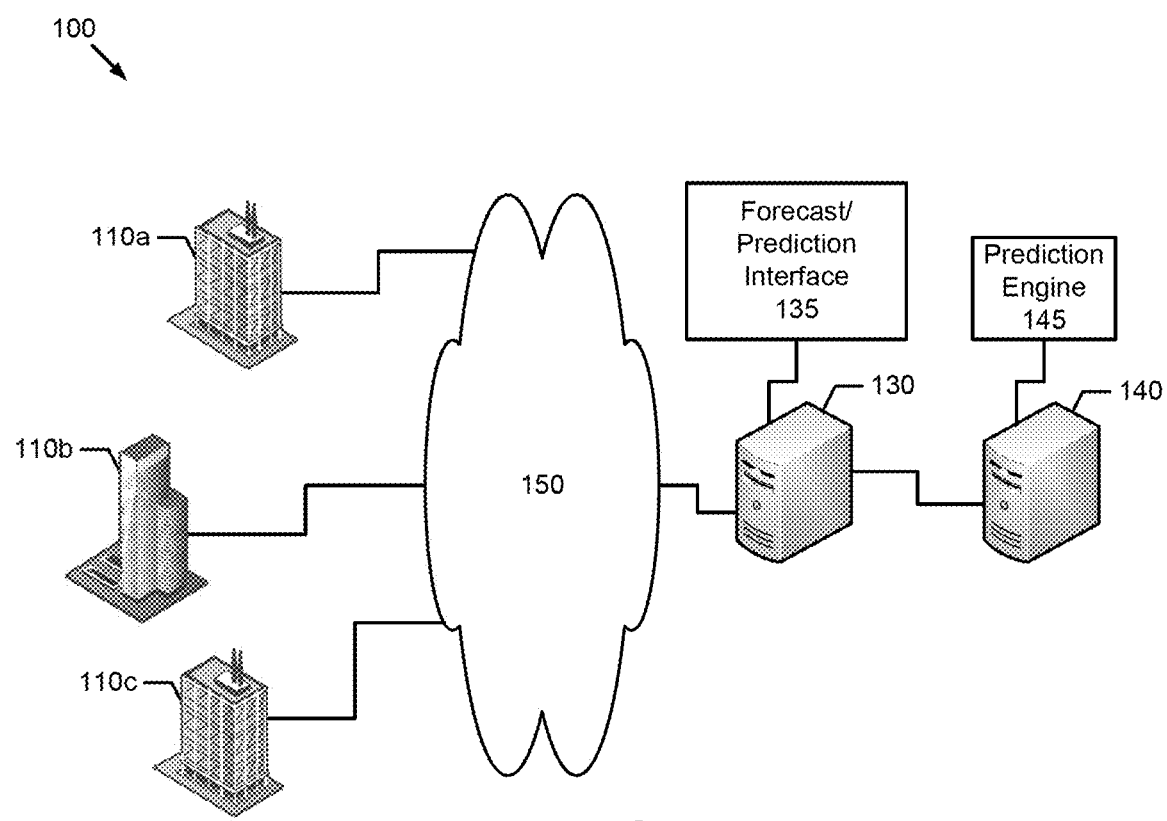
FIG. 1 is a block diagram that illustrates a communication network including an Artificial Intelligence (AI) assisted event prediction system in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

Embodiments of the inventive concept are described herein in the context of a prediction engine that includes a machine learning engine and an artificial intelligence (AI) engine. It will be understood that embodiments of the inventive concept are not limited to a machine learning implementation of the prediction engine and other types of AI systems may be used including, but not limited to, a multi-layer neural network, a deep learning system, a natural language processing system, and/or computer vision system Moreover, it will be understood that the multi-layer neural network is a multi-layer artificial neural network comprising artificial neurons or nodes and does not include a biological neural network comprising real biological neurons.

Some embodiments of the inventive concept stem from a realization that variations in the way that medical claims are processed for payment by payors (e.g., insurers) both between payors and/or between the types of services being invoiced may make it difficult for a provider to forecast or estimate future collections. Providers may often make generalized assumptions that a medical claim will be processed and payment received within a specified time from the date that the claim is issued. But such a generalized assumption may not account for variations between payors, service providers, or other factors and may result in an inaccurate forecast that makes managing the medical facility or practice more difficult. Embodiments of the inventive concept may provide an Artificial Intelligence (AI) assisted event prediction system that may receive information associated with a stimulus, which may be, for example, information associated with a medical claim for services provided to a patient and information associated with a provider that provided the services to the patient. An AI engine may be used to predict when an event will occur in response to the stimulus. For example, the AI engine may predict when the payment will be received for the claim and in what amount, e.g., in full or in part, or may predict whether the payment will not be received due to denial of the claim. The information associated with the medical claim may include an identifier for the payor, billing code for one or more services provided at an encounter and a date at which the medical claim was submitted to the payor. As a result, the AI engine may predict the amount and timing of the payment based on learned historical information for the payor and learned historical information on the type of service provided to the patient. For example, some payors may be more prompt than others in payment, some payors may be more likely to pay a reduced amount and request a reduction in an invoice, and/or some types of services provided may be subject to more or less scrutiny affecting the timing and/or the amount of payment for such services. The additional granularity in predicting events, such as claim payments, may allow health care providers to better manage their facilities and practices by selecting which payors (e.g., insurance providers) to accept, advising patients on which procedures may not be reimbursed by a payor, and/or identifying root causes for potential underpayment or overpayment by payors. A health care facility or practice may also adjust what specialties or services it provides if some types of specialties are predicted to result in a loss for the facility or practice.

Although described herein in the context of predicting events, such as the timing and amounts of payments of medical claims submitted by medical service provider, the AI assisted event prediction system can be used in other contexts in accordance with other embodiments of the inventive concept including, but not limited to, agriculture, manufacturing, scientific research, retailing, and other endeavors. For example, with respect to agriculture, the AI assisted event prediction system may be used to predict yield based on factors, such as fertilizer, crop plant date, rain amounts, and sun amounts. With respect to manufacturing, the AI assisted event prediction system may be used to predict product output based on timing of arrival of various parts and components used in the manufacturing process and the historical downtime of machines used in manufacturing the product. With respect to retailing, the AI assisted event prediction system may be used to predict sales based on advertising, holidays, sale pricing, and other factors. With respect to scientific research, hypotheses may be generated as a prediction based on historical data associated with one or more phenomena.

Referring to FIG. 1, a communication network 100 including an AI assisted event prediction system, in accordance with some embodiments of the inventive concept, comprises a plurality of health care provider facilities or practices 110a, 110b, and 110c that are coupled to an AI assisted event prediction system including a forecast/prediction server 130 and a prediction engine server 140. The health care provider facilities or practices 110a, 110b, and 110c may represent various types of organizations that are used to deliver health care services to patients, which are referred to generally herein as "providers." The providers may include, but are not limited to, hospitals, medical practices, mobile patient care facilities, diagnostic centers, lab centers, and the like. The providers may operate by providing health care services for patients and then invoicing one or more payors for the services rendered. The payors may include, but are not limited to, private insurance plans, government insurance plans (e.g., Medicare, Medicaid, state or federal public employee insurance plans), hybrid insurance plans (e.g., Affordable Care Act plans), private medical cost sharing plans, and the patients themselves.

According to some embodiments of the inventive concept, providers may access the AI assisted event prediction system to allow them to forecast or predict the timing and amounts of payments for claims generated for services provided to patients. The AI assisted event prediction system may include a forecast/prediction interface server 130, which includes a forecast/prediction interface module 135 to facilitate the transfer of medical claim and provider information between the respective providers 110a, 110b, and 110c, and a prediction engine server 140, which includes a prediction engine module 145. The prediction engine server 140 and prediction engine module 145 may be configured to receive medical claim information and provider information from the providers 110a, 110b, and 110c by way of the forecast/prediction interface server 130 and forecast/prediction interface module 135. The forecast/prediction interface module 135 in conjunction with the prediction engine module 145 may be further configured to generate a prediction about when an event will occur, such as the timing and amount of a payment for a medical claim for services, in response to a stimulus, such as the generation of the medical claim for services and accompanying information associated with the medical claim and information associated with the provider.

It will be understood that the division of functionality described herein between the prediction engine server 140/prediction engine module 145 and the forecast/prediction interface server 130/forecast/prediction interface module 135 is an example. Various functionality and capabilities can be moved between the prediction engine server 140/prediction engine module 145 and the forecast/prediction interface server 130/forecast/prediction interface module 135 in accordance with different embodiments of the inventive concept. Moreover, in some embodiments, the prediction engine server 140/prediction engine module 145 and the forecast/prediction interface server 130/forecast/prediction interface module 135 may be merged as a single logical and/or physical entity.

A network 150 couples the providers 110a, 110b, and 110c to the forecast/prediction interface server 130/forecast/prediction interface module 135. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The forecast/prediction service provided through the forecast/prediction interface server 130, forecast/prediction interface system module 135, prediction engine server 140, and prediction engine module 145, in some embodiments, may be embodied as a cloud service. For example, providers may integrate their claims generation systems with the AI assisted event prediction service and access the service as a Web service. In some embodiments, the AI assisted event prediction service may be implemented as a Representational State Transfer Web Service (RESTful Web service). The forecast/prediction interface system module 135 may further provide an interface for communicating the predictions generated by the prediction engine server 140/prediction engine module 145 to, for example, a health care practice or facility manager. The interface may be embodied in a variety of ways including, but not limited to, an Application Programming Interface (API), one or more tables, one or more graphs/charts, a screen with one or more panes of text and/or graphic information, or the like. The predictive information conveyed to a health care practice or facility manager may assist the manager in identifying areas on which the practice or facility is underperforming, which may allow the practice or facility manager to take corrective action with respect to the underlying causes of the underperformance earlier and with greater precision or accuracy than would otherwise be possible when using postmortem reports and analysis as a basis for such corrective action.

Although FIG. 1 illustrates an example communication network including an AI assisted event prediction system for predicting the timing and/or amount of payment of a claim generated for a provided medical service, it will be understood that embodiments of the inventive subject matter are not limited to such configurations, but are intended to encompass any configuration capable of carrying out the operations described herein.

Figure 2:
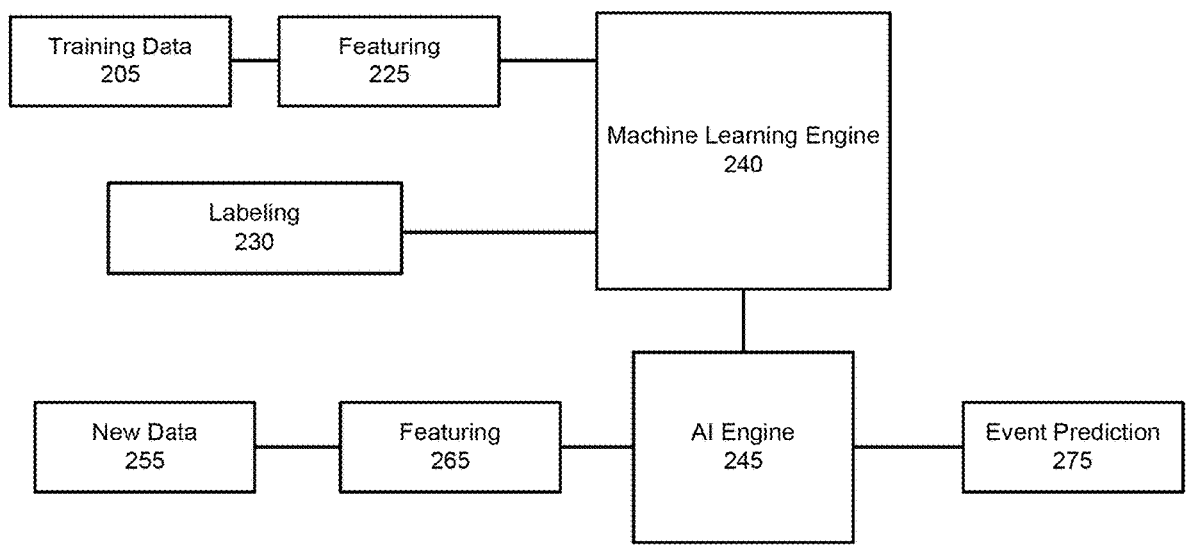
FIG. 2 is a block diagram of the AI assisted event prediction system of FIG. 1 in accordance with some embodiments of the inventive concept.

FIG. 2 is a block diagram of the prediction engine 145 used in the AI assisted event prediction system in accordance with some embodiments of the inventive concept. As shown in FIG. 2, the prediction engine 145 may include both training modules and modules used for processing new data on which to make event predictions. The modules used in the training portion of the prediction engine 145 include the training data 205, the featuring module 225, the labeling module 230, and the machine learning engine 240. The training data 205 may comprise information associated with a stimulus that may trigger an event. In some embodiments of the inventive concept, the training data may comprise information associated with medical claims for services provided to one or more patients along with information associated with the one or more providers that provided the services to the one or more patients. The featuring module 225 is configured to identify the individual independent variables that are used by the prediction engine 145 to make predictions, which may be considered a dependent variable. For example, the training data 205 may be generally unprocessed or formatted and include extra information in addition to medical claim information and provider information. For example, the medical claim data may include account codes, business address information, and the like, which can be filtered out by the featuring module 225. The features extracted from the training data 205 may be called attributes and the number of features may be called the dimension. The labeling module 230 may be configured to assign defined labels to the training data and to the generated predictions to ensure a consistent naming convention for both the input features and the predicted outputs. The machine learning engine 240 may process both the featured training data 205, including the labels provided by the labeling module 230, and may be configured to test numerous functions to establish a quantitative relationship between the featured and labeled input data and the predicted outputs. The machine learning engine 240 may use modeling techniques to evaluate the effects of various input data features on the predicted outputs. These effects may then be used to tune and refine the quantitative relationship between the featured and labeled input data and the predicted outputs. The tuned and refined quantitative relationship between the featured and labeled input data generated by the machine learning engine 240 is output for use in the AI engine 245. The machine learning engine 240 may be referred to as a machine learning algorithm.

The modules used for processing new data on which to make event predictions include the new data 255, the featuring module 265, the AI engine module 245, and the event prediction module 275. The new data 255 may be the same data/information as the training data 205 in content and form except the data will be used for an actual event forecast or prediction. Likewise, the featuring module 265 performs the same functionality on the new data 255 as the featuring module 225 performs on the training data 205. The AI engine 245 may, in effect, be generated by the machine learning engine 240 in the form of the quantitative relationship determined between the featured and labeled input data and the predicted outputs. The AI engine 245 may, in some embodiments, be referred to as an AI model. The AI engine 245 may be configured to output predicted events via the event prediction module 275. The event prediction module 275 may be configured to communicate the event prediction in a variety of formats and may include additional information, including, but not limited to, illustrations of the event in comparisons to an idealized version of the event, comparison of the event outcome relative to one or more of the featured inputs, and trends in the event outcomes including a breakdown of such trends relative to one or more of the featured inputs. In some embodiments, the predicted events are generated based on stimulus, such as medical claim and provider information. The predicted events may include, for example, the timing and/or amount of payment for the various medical claims that have been filed or submitted with one or more payors.

Figure 3:
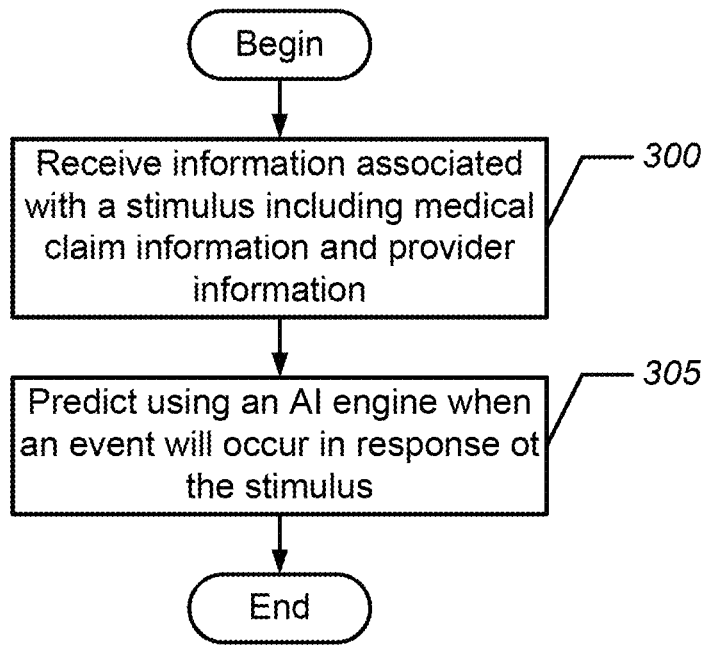
FIGS. 3-7 are flowcharts that illustrate operations for predicting events based on medical service and provider information using the AI assisted event prediction system of FIG. 1 in accordance with some embodiments of the inventive concept.

FIGS. 3-7 are flowcharts that illustrate operations for predicting events based on medical service and provider information using an AI assisted event prediction system in accordance with some embodiments of the inventive concept. Referring now to FIG. 3, operations begin at block 300 where the AI engine 245 receives information associated with a stimulus including, for example, medical claim information for services provided to one or more patients and provider information for the provider that provided the medical services to the patient(s). The AI engine 245 may then predict when an event will occur in response to the stimulus at block 305. The medical claim information may include for each medical claim an identifier for a payor, a billing code for an encounter, and/or a date at which the medical claim was submitted to the payor. The information associated with the provider may include an identifier for the provider and/or a provider specialty. The stimulus may comprise a filing of one or more medical claims with the payor(s) and an event may comprise the payment of a medical claim by a payor.

Figure 4:
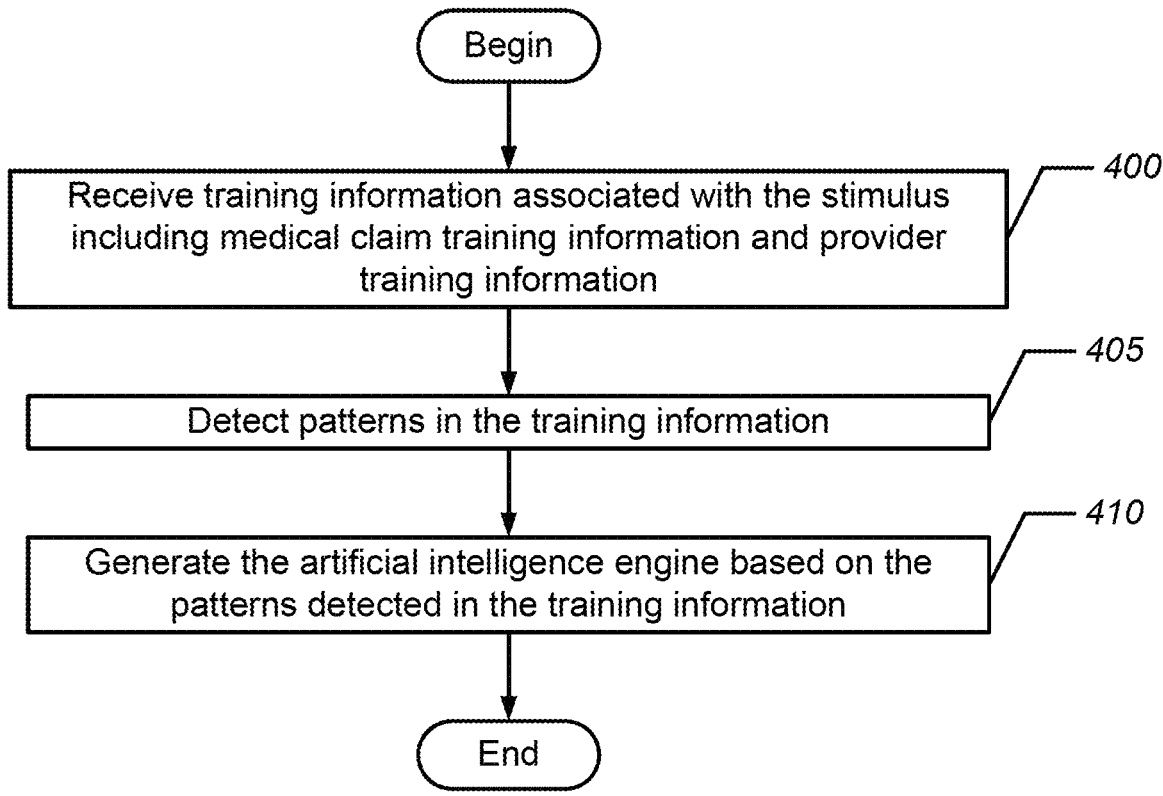

As described above with respect to FIG. 2, the prediction engine 145 may include both training modules and modules used for processing new data on which to make event predictions. The modules used in the training portion of the prediction engine 145 include the training data 205, the featuring module 225, the labeling module 230, and the machine learning engine 240. Referring now to FIG. 4, the machine learning engine 240 is configured to receive training information associated with the stimulus including medical claim training information associated with a plurality of medical claims for services provided to a plurality of patients and provider training information associated with a plurality of providers that provided the services to the plurality of patients. The training information for both the medical claims and the providers may comprise historical data for medical claims filed by providers with payors and the timing and amounts of the payment of these invoices by the payors. At block 405 the machine learning engine 240 may detect patterns in the training information associated with the stimulus. The machine learning engine 240 may then generate the AI engine 245 at block 410 based on the patterns detected in the training information associated with the stimulus.

In some embodiments of the inventive concept, the medical claim training information may include, but is not limited to, identifiers for each of the payors, respectively, billing codes for each of the encounters between patients and the providers, respectively, and/or the dates at which the medical claims were submitted to the payors, respectively. Moreover, in some embodiments, the medical claim training information may include a classification of the claims into multiple categories. For example, the medical claims may be classified into those claims for which payment from a payor has been received in full, those claims for which payment from a payor has been received in partial satisfaction of the amount invoiced (i.e., a payment amount that is less than the amount invoiced via the claim), and those claims for which payment has not been received. The medical claim training information may include the dates at which payment is received for the claims in which payment is received in full or in part. The medical claim training information may also include any amount of deficiency when the payment is less than the invoiced amount of the claim. An identifier for the payor may be included as part of the medical information for any medical claim whether paid in full, paid in part, or not paid at all.

In some embodiments of the inventive concept, the medical claim training information may further include an age associated with each of the medical claims that corresponds to a difference between a date at which the medical claim was submitted or filed with a payor and the date at which a payment for the claim (whether payment in full or in part) was received from the payor.

In some embodiments of the inventive concept, the provider information may include an identifier for each of the provider(s) and/or a specialty for each of the provider(s).

Figure 5:
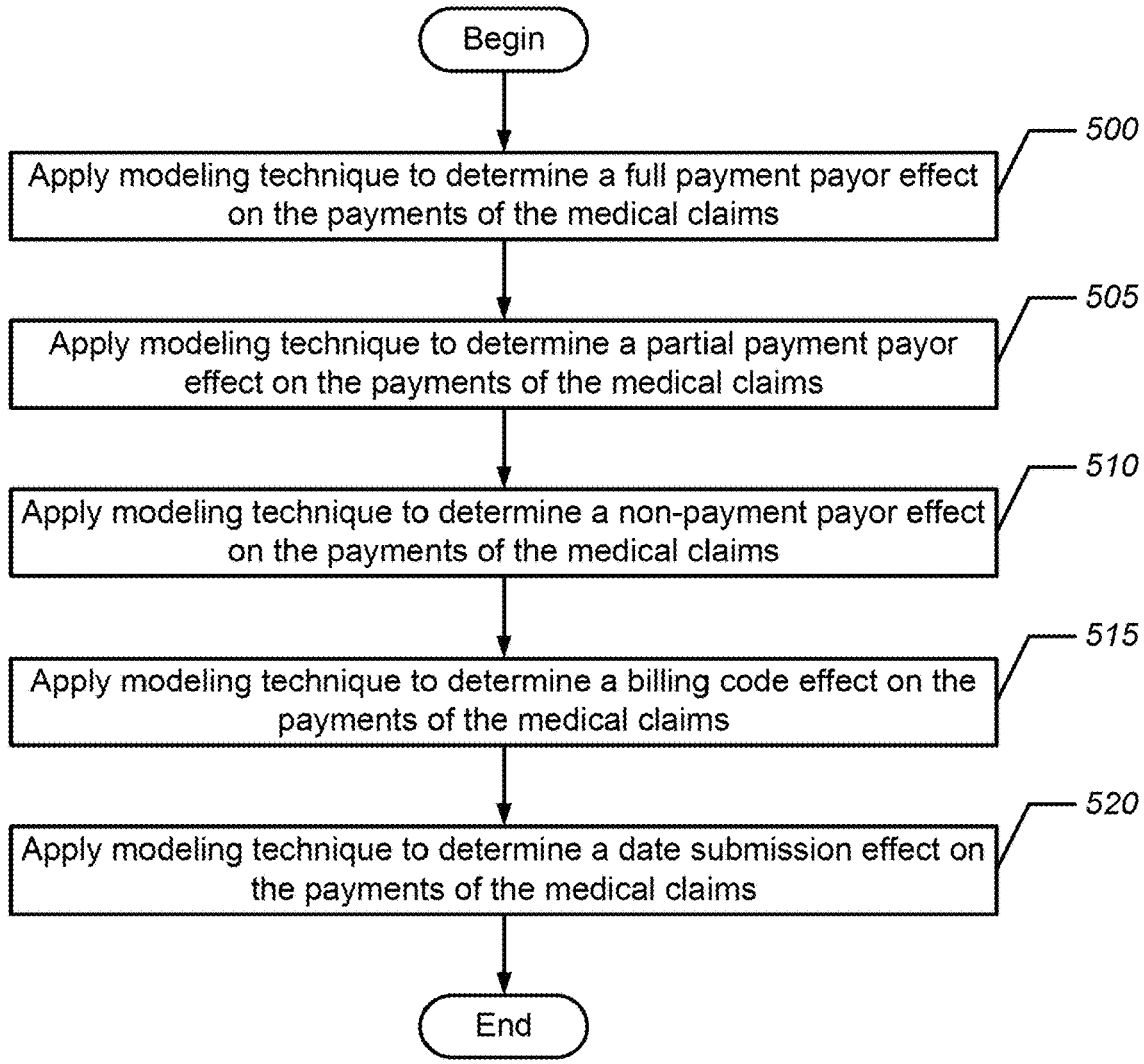

As described above, the machine learning engine 240 may process both the featured training data 205, including the labels provided by the labeling module 230, and may be configured to establish a quantitative relationship between the featured and labeled input data and the predicted outputs. As illustrated in FIG. 5, modeling techniques may be used on the medical claim training information to evaluate the effects of various input data features on the predicted outputs and these effects may be used to tune, refine, and/or adjust the AI engine 245, which is generated by the machine learning engine 240. Referring now to FIG. 5, operations begin at block 500 where the machine learning engine 240 applies a modeling technique to the medical claim payments and those payors that paid medical claims in full to determine a full payment payor effect on the payments of the medical claims. At block 505, a modeling technique is applied the medical claim payments and those payors that paid medical claims in partial satisfaction of the amount invoiced to determine a partial payment payor effect on the payments of the medical claims. At block 510 a modeling technique is applied to the medical claim payments and those payors that did not provide any payment of the invoiced amount to determine a non-payment payor effect on the payments of the medical claims. At block 515 a modeling technique is applied to the medical claim payments and the billing codes, which may correspond to procedures, treatments, medications, etc., to determine a billing code effect on the payments of the medical claims. At block 520 a modeling technique is applied to the medical claim payments and the dates at which the medical claims were submitted or filed with the payors for payment to determine a date submission effect on the payments of the medical claims. The modeling technique may be embodied in various ways in accordance including, but not limited to, a regression technique, a neural network technique, an Autoregressive Integrated Moving Average (ARIMA) technique, a deep learning technique, a linear discriminant analysis technique, a decision tree technique, a naïve Bayes technique, a K-nearest neighbors technique, a learning vector quantization technique, a support vector machine technique, and/or a bagging/random forest technique. One or more of each of these techniques may be used in any of the operations of blocks 500, 505, 510, 515, and/or 520. Moreover, the modeling technique used for any one of the blocks 500, 505, 510, 515, and 520 may be the same or different than the modeling technique used for any other one of the blocks 500, 505, 510, 515, and 520. The machine learning engine 240 may generate the AI engine 245 based on the full payment payor effect, the partial payment payor effect, the non-payment payor effect, the billing code effect, and/or the date submission effect.

Figure 6:
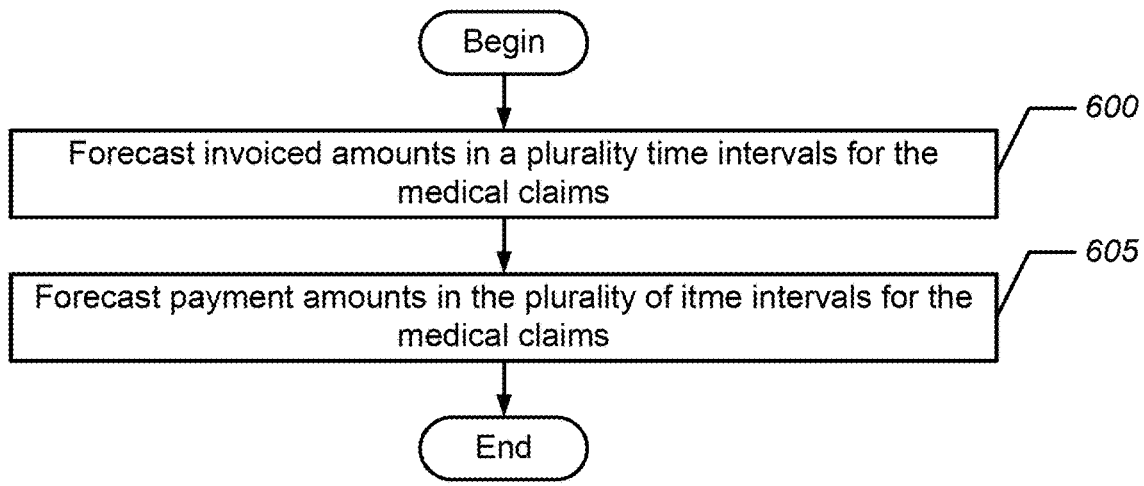
Figure 8:
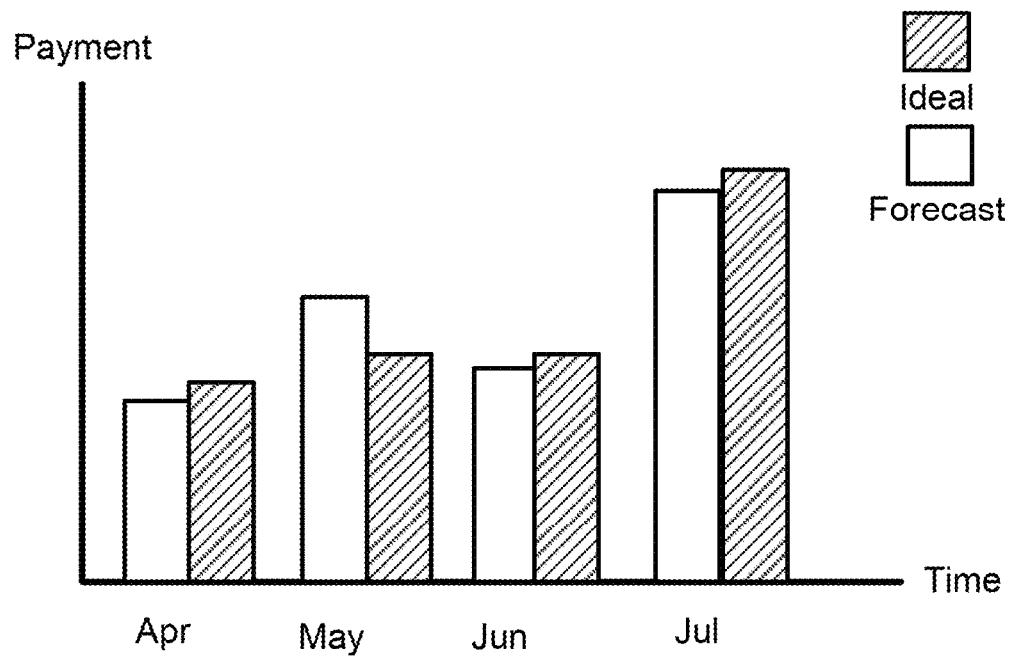
FIGS. 8-10 are charts that illustrate predicted events over a time interval based on medical service and provider information using the AI assisted event prediction system of FIG. 1 in accordance with some embodiments of the inventive concept.

As described above, the AI engine 245 may be configured output predicted events based on new stimulus data or information via the event prediction module 275. Referring now to FIG. 6, the AI engine 245 may predict or forecast invoiced amounts for a plurality of medical claims in a plurality of time intervals at block 600 based on the dates at which the medical claims were submitted for payment. The AI engine 245 may also predict or forecast payments from one or more payors in the plurality of time intervals at block 605 based on the dates at which procedures, treatments, lab work, medications administered, etc. corresponding to billing codes were performed/administered. This is illustrated, for example, in FIG. 8, which shows aggregated forecast or predicted medical claim payments for one or more payors across a four-month time intervals spanning April through July. Also illustrated is an ideal payment amount that is determined for each month, which may be based, for example, one or more defined assumptions regarding the payment timeline and amount. For example, a rule may be defined for computing ideal payment timing and amounts in which a claim will be assumed to be paid within a certain number of days at a certain percentage recovery rate (e.g., payment within 90 days at an assumed recovery rate of 90% of the invoiced amount). The ideal payment amounts are shown in FIG. 8 as the cross-hatched bars with the predicted payment amounts being represented by the bars without the cross-hatching.

Figure 7:
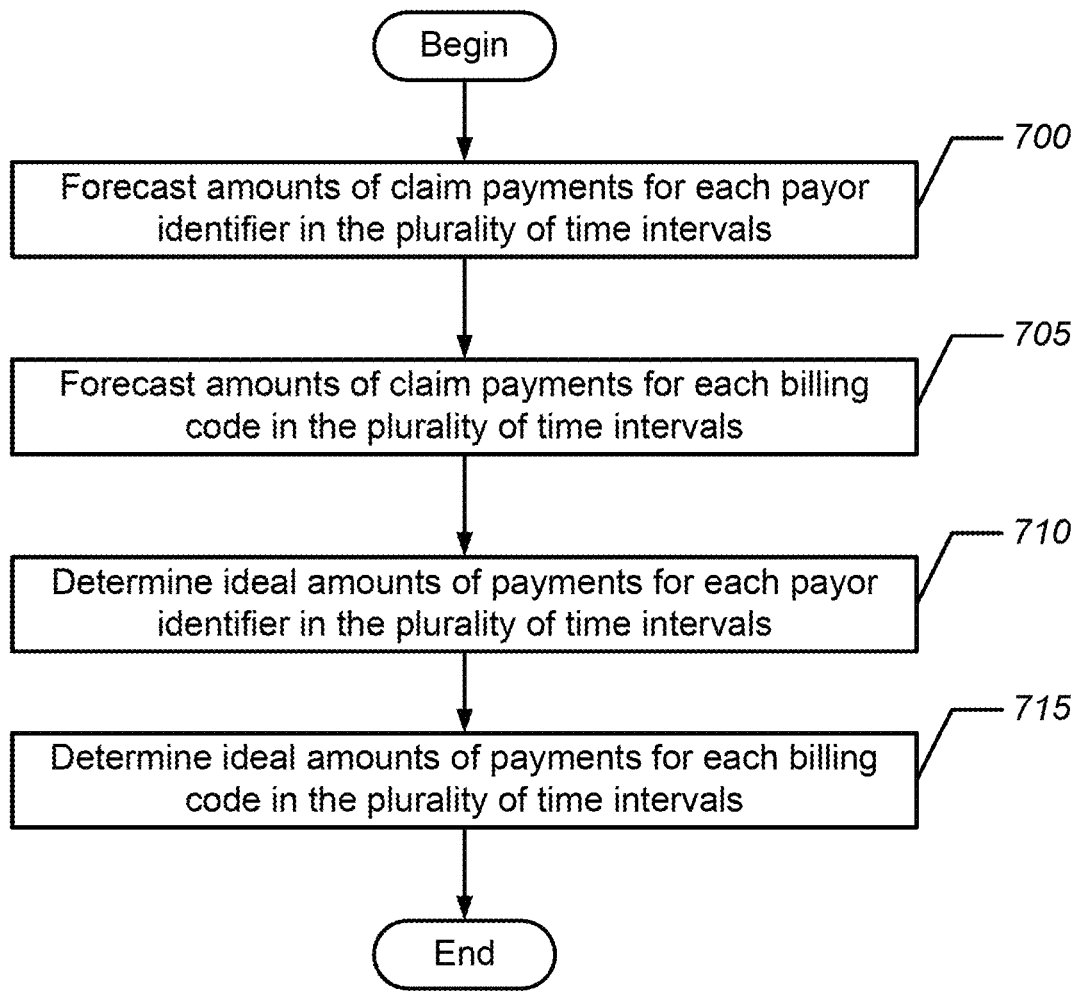
Figure 9:
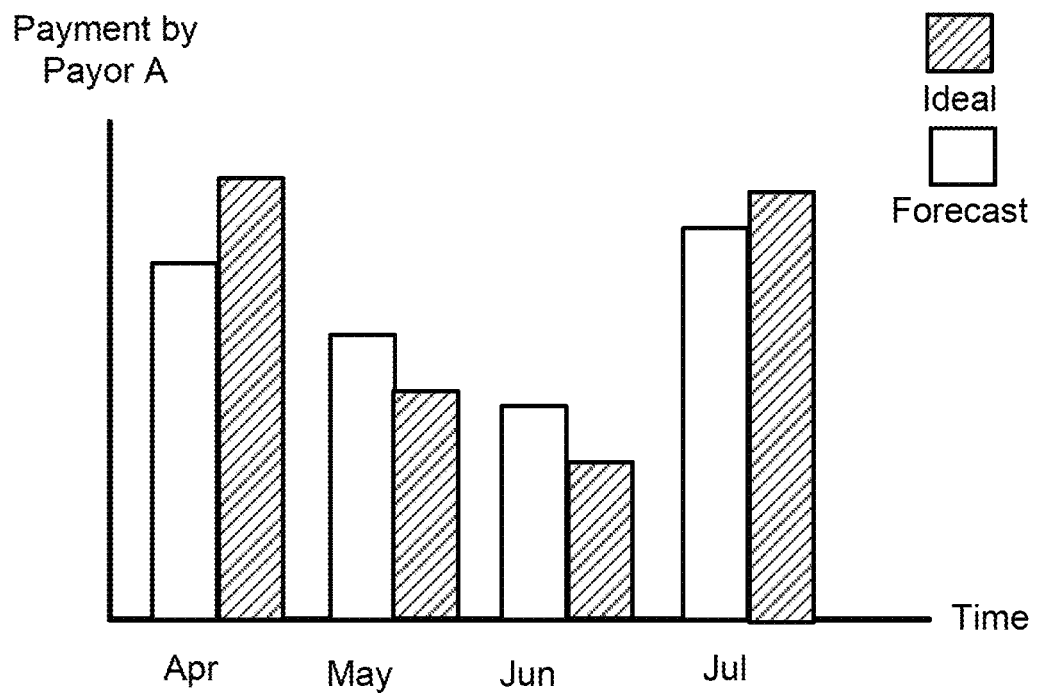
Figure 10:
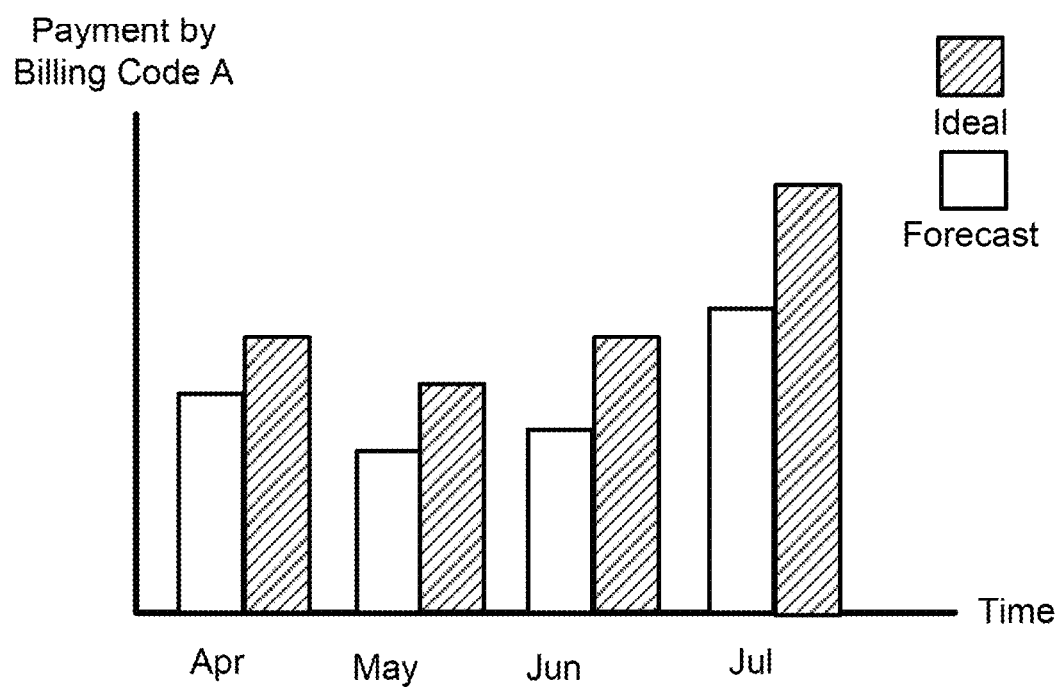

Embodiments of the inventive concept, therefore, may allow a medical practice or facility manager to predict forecast future payment of invoices for multiple payors across time interval and compare such a forecast to an idealized or preferred payment schedule for the payors to identify time periods where there may be shortfalls and time periods where receipts may exceed an idealized amount. Trends can be discerned from the forecast payments over the time interval and areas it may help facility or practice managers to identify areas to target to provide a less volatile payment schedule or areas that are not economically profitable for the facility or practice. In this regard, as illustrated in FIGS. 7, 9, and 10, a forecast of payments may be broken down by individual payor and/or billing code for example to assist in identifying trends and patterns at a more granular level. Payors that are problematic in terms of payment timing or amount may be identified. Likewise, practice areas or procedures that are represented by specific billing codes may be identified as resulting in lengthy delays for payment and or reduced payment amounts. Prompt payors and profitable practice areas/procedures may be similarly identified.

Referring now to FIG. 7, operations begin at block 700 in which medical claim payments for each payor identifier is predicted or forecast over a plurality of time intervals, e.g., over a plurality of months, based on the dates in which the medical claims were submitted to each payor. At block 705, medical claim payments for each billing code are predicted or forecast over the plurality of time intervals. As described above, ideal payment amounts may be determined for each of the payors and/or billing codes over the time intervals at blocks 710 and 715, respectively. FIGS. 9 and 10 illustrate forecast or predicted payments from a single Payor A over the monthly time intervals April through July, which are represented by the bars without the cross-hatching, and forecast or predicted payments for a single billing code A over the same monthly time intervals, which are also represented by the bars without the cross-hatching, respectively. FIGS. 9 and 10 also illustrate an idealized payment schedule for Payor A and billing code A, respectively, which are represented by the bars with the cross-hatching. As shown in FIG. 9, the forecast payments for Payor A are less than the ideal amounts in April and July, but exceed the ideal amounts in May and June. Billing code A, however, appears to be problematic in terms of payment as the forecast or predicted payments for this billing code fall short of the idealized amounts in each month. FIGS. 9 and 10 are examples of how forecasting medical claim payments can be broken down into a more granular level rather than using a traditional waterfall approach to predicting payment of medical claims based solely or primarily on the date that a medical claim was filed. The granularity can be increased in a variety of ways beyond those explicitly illustrated in FIGS. 7-10. For example, medical claim payments may be forecast based on both individual payor identification and billing code for example to determine if a particular billing code frequently results in payment delays for a particular payor, but not for other payors.

Figure 11:
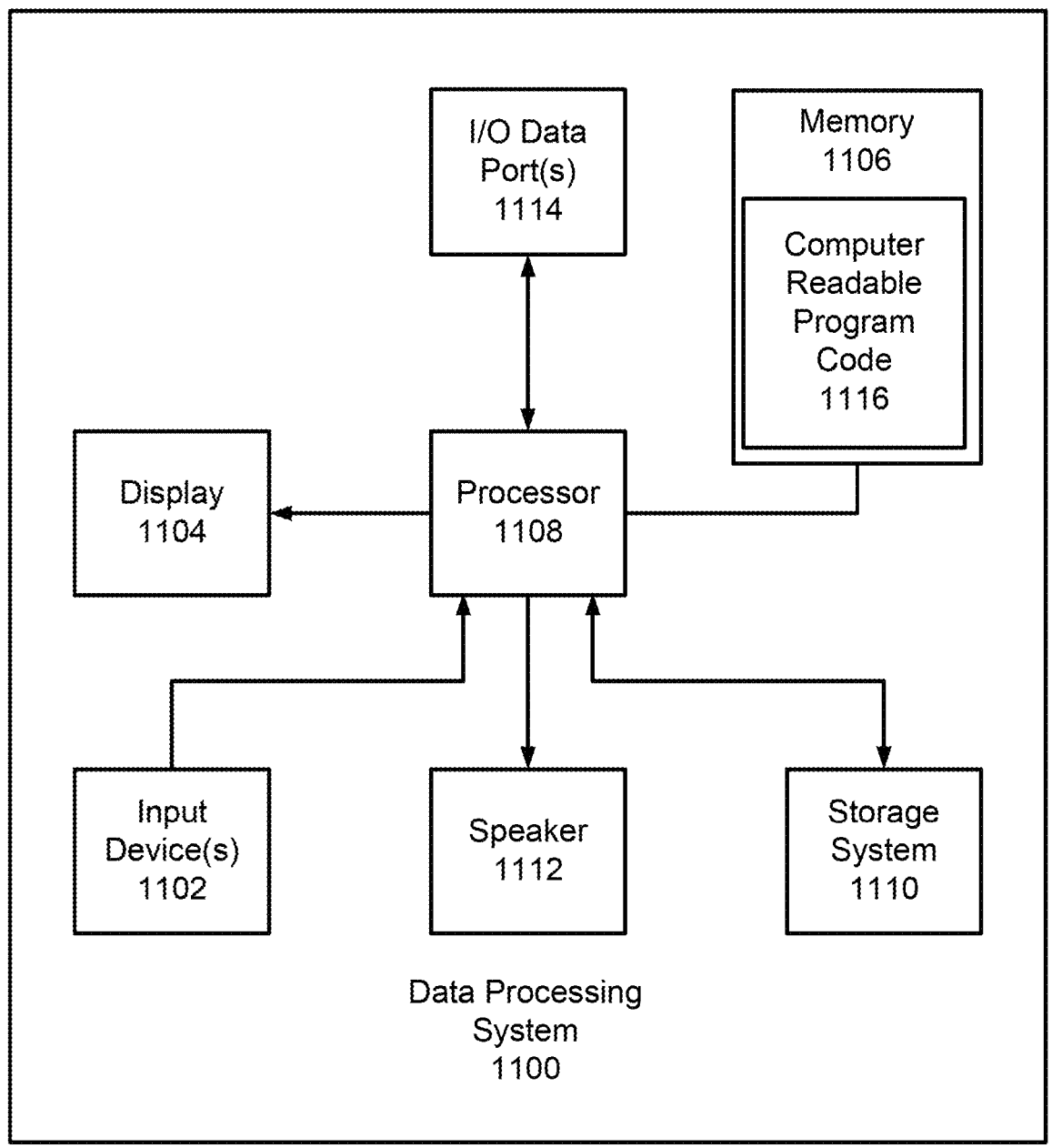
FIG. 11 is a data processing system that may be used to implement one or more servers in the AI assisted event prediction system of FIG. 1 in accordance with some embodiments of the inventive concept.

Referring now to FIG. 11, a data processing system 1100 that may be used to implement the prediction engine server 140 of FIG. 1, in accordance with some embodiments of the inventive concept, comprises input device(s) 1102, such as a keyboard or keypad, a display 1104, and a memory 1106 that communicate with a processor 1108. The data processing system 1100 may further include a storage system 1110, a speaker 1112, and an input/output (I/O) data port(s) 1014 that also communicate with the processor 1108. The processor 1108 may be, for example, a commercially available or custom microprocessor. The storage system 1110 may include removable and/or fixed media, such as floppy disks, ZIP drives, hard disks, or the like, as well as virtual storage, such as a RAMDISK. The I/O data port(s) 1114 may be used to transfer information between the data processing system 1100 and another computer system or a network (e.g., the Internet). These components may be conventional components, such as those used in many conventional computing devices, and their functionality, with respect to conventional operations, is generally known to those skilled in the art. The memory 1106 may be configured with computer readable program code 1116 to facilitate AI assisted event prediction according to some embodiments of the inventive concept.

Figure 12:
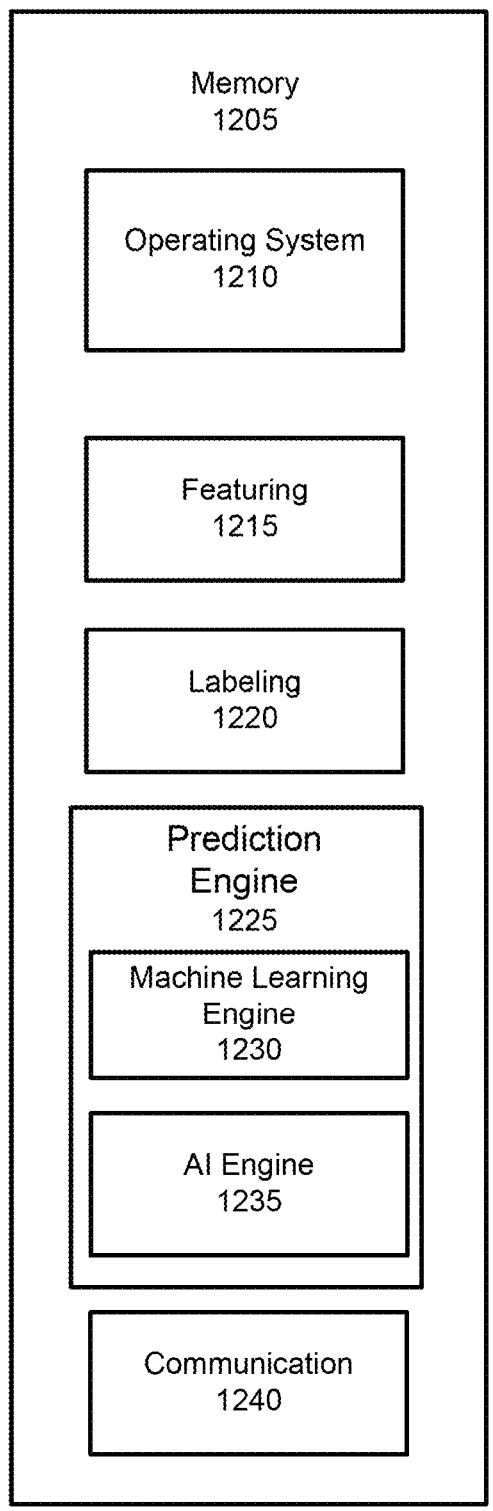
FIG. 12 is a block diagram that illustrates a software/hardware architecture for use in the AI assisted event prediction system of FIG. 1 in accordance with some embodiments of the inventive concept.

FIG. 12 illustrates a memory 1205 that may be used in embodiments of data processing systems, such as the prediction engine server 140 of FIG. 1 and the data processing system 1100 of FIG. 11, respectively, to facilitate AI assisted event prediction according to some embodiments of the inventive concept. The memory 1205 is representative of the one or more memory devices containing the software and data used for facilitating operations of the prediction engine server 140 and prediction engine 145 as described herein. The memory 1205 may include, but is not limited to, the following types of devices: cache, ROM, PROM, EPROM, EEPROM, flash, SRAM, and DRAM. As shown in FIG. 12, the memory 1205 may contain five or more categories of software and/or data: an operating system 1210, a featuring module 1215, a labeling module 1220, a prediction engine module 1225, and a communication module 1240. In particular, the operating system 1210 may manage the data processing system's software and/or hardware resources and may coordinate execution of programs by the processor. The featuring module 1215 may be configured to perform one or more of the operations described above with respect to the featuring modules 225, 265, the flowcharts of FIGS. 3-7, and the charts of FIGS. 8-10. The labeling module 1220 may be configured to perform one or more of the operations described above with respect to the labeling module 230, the flowcharts of FIGS. 3-7, and the charts of FIGS. 8-10. The prediction engine 1225 may comprise a machine learning engine module 1230 and an AI engine module 245. The machine learning engine module 1230 may be configured to perform one or more operations described above with respect to the machine learning engine 240, the flowcharts of FIGS. 3-7, and the charts of FIGS. 8-10. The AI engine module 1235 may be configured to perform one or more operations described above with respect to the AI engine 245, the flowcharts of FIGS. 3-7, and the charts of FIGS. 8-10. The communication module 1240 may be configured to support communication between, for example, the prediction engine server 140 and the forecast/prediction interface server 130 and/or providers 110a, 110b, and 110c.

Although FIGS. 11-12 illustrate hardware/software architectures that may be used in data processing systems, such as the prediction engine server 140 of FIG. 1 and the data processing system 1100 of FIG. 11, respectively, in accordance with some embodiments of the inventive concept, it will be understood that embodiments of the present invention are not limited to such a configuration but is intended to encompass any configuration capable of carrying out operations described herein.

Computer program code for carrying out operations of data processing systems discussed above with respect to FIGS. 1-12 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the prediction engine server 140 of FIG. 1 and the data processing system 1100 of FIG. 11 may each be implemented as a single processor system, a multi-processor system, a multi-core processor system, or even a network of standalone computer systems, in accordance with various embodiments of the inventive concept. Each of these processor/computer systems may be referred to as a "processor" or "data processing system."

The data processing apparatus described herein with respect to FIGS. 1-12 may be used to facilitate AI assisted event prediction according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 1205 when coupled to a processor includes computer readable program code that, when executed by the processor, causes the processor to perform operations including one or more of the operations described herein with respect to FIGS. 1-10.

Some embodiments of the inventive concept described herein may provide an AI assisted event prediction system that may forecast or predict when an event will occur in response to a stimulus. The event prediction system may be used in many different contexts and technological areas including the delivery of healthcare services and management of healthcare facilities and practices. The event prediction system may be trained using historical records, i.e., medical claims, generated for invoicing payors for the delivery of health care services and products by providers with the health care services and products being identified by billing codes. The AI assisted event prediction system may allow a health care facility or practice to improve the management of their organization and delivery of health care services and products through improved forecasting for payor invoice payment and timing. Areas in which the organization may be performing poorly may be predicted in advance and with greater insight on potential sources of the poor performance. For example, medical claim payments may be forecast based on payor, billing code, or other factors including combinations of factors to allow the organization to mitigate the potential sources of problems earlier than may be possible when "waterfall" techniques are used to forecast medical claim payments for all payors together. Thus, the economic performance of the health care facility or practice may be predicted and a determination made whether to take actions for improvement should they be warranted based on the forecast.

Further Definitions and Embodiments

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A method, comprising:

receiving information associated with a stimulus, the stimulus comprising a filing of a medical claim with a payor, the information associated with the stimulus comprising first information associated with a medical claim for services provided to a patient and second information associated with a provider that provided the services to the patient;

generating, using a machine learning engine, an artificial intelligence engine; and predicting, using the artificial intelligence engine, when an event will occur in response to the stimulus, the event comprises payment of the medical claim by the payor;

wherein generating the artificial intelligence engine comprises:

receiving training information associated with the stimulus, the training information associated with the stimulus comprising first training information associated with a plurality of medical claims for services provided to a plurality of patients, respectively, the first training information comprising payment information associated with the plurality of medical claims, and second training information associated with a plurality of providers that provided the services to the plurality of patients;

detecting patterns in the training information associated with the stimulus;

training the machine learning engine based on the detected patterns detected in the training information associated with the stimulus; and generating the artificial intelligence engine based on the machine learning engine that has been trained.

2. The method of claim 1, wherein the first information associated with the medical claim comprises an identifier for a payor, a billing code for an encounter, and/or a date at which the medical claim was submitted to the payor; and wherein the second information associated with the provider comprises an identifier for the provider and/or a provider specialty.

3. The method of claim 1, wherein the first training information associated with the plurality of medical claims comprises a plurality of identifiers for a plurality of payors, respectively, a plurality of billing codes for a plurality of encounters, respectively, a plurality of dates at which the plurality of medical claims were submitted to the plurality of payors, identifications of first ones of the plurality of medical claims for which a first plurality of payments were received from first ones of the plurality of payors in full satisfaction of invoiced amounts on the first ones of the plurality of medical claims, a first plurality of dates at which the first plurality of payments were received from first ones of the plurality of payors, identifications of second ones of the plurality of medical claims for which a second plurality of payments were received from second ones of the plurality of payors in amounts less than invoiced amounts on the second ones of the plurality of medical claims, respectively, a second plurality of dates at which the second plurality of payments were received from the second ones of the plurality of payors, identifications of third ones of the plurality of medical claims for which payments were never received from third ones of the plurality of payors, and a plurality of deficiencies corresponding to differences between the amounts less than the invoiced amounts and the invoiced amounts; and wherein the second training information associated with the plurality of providers comprises a plurality of identifiers for the plurality of providers, respectively, and/or a plurality of specialties for the plurality of providers, respectively.

4. The method of claim 3, wherein the first training information further comprises a plurality of ages associated with the plurality of medical claims, the plurality of ages comprising a plurality of differences between the plurality of dates at which the plurality of medical claims were submitted to the plurality of payors and the first plurality of dates at which the first plurality of payments were received from the plurality of payors and the second plurality of dates at which the second plurality of payments were received from the plurality of payors.

5. The method of claim 4, wherein the event comprises a plurality of events corresponding to payments of the plurality of medical claims by the plurality of payors, respectively, the method further comprising:

applying a first modeling technique to the first plurality of payments and the first ones of the plurality of payors to determine a first payor effect on the payments of the plurality of medical claims;

applying a second modeling technique to the second plurality of payments and the second ones of the plurality of payors to determine a second payor effect on the payments of the plurality of medical claims;

applying a third modeling technique to the third ones of the plurality of medical claims for which payments were never received and the third ones of the plurality of payors to determine a third payor effect on the payments of the plurality of medical claims;

applying a fourth modeling technique to the payments of the plurality of medical claims and the plurality of billing codes to determine a billing code effect on the payments of the plurality of medical claims; and applying a fifth modeling technique to the payments of the plurality of medical claims and the plurality of dates at which the medical claims were submitted to the plurality of payors to determine a date submission effect on the payments of the plurality of medical claims.

6. The method of claim 5, wherein generating the artificial intelligence engine further comprises:

generating the artificial intelligence engine based on the first payor effect, the second payor effect, the third payor effect, the billing code effect, and the date submission effect.

7. The method of claim 1, wherein the first information is further associated with a plurality of medical claims for services provided to a plurality of patients and the second information is further associated with a plurality of providers that provided the services to the plurality of patients;

wherein the stimulus comprises filing of a plurality of medical claims with a plurality of payors;

wherein the event comprises a plurality of events corresponding to payments of the plurality of medical claims by the plurality of payors, respectively; and wherein predicting when the event will occur in response to the stimulus comprises predicting, using the artificial intelligence engine, when the plurality of events will occur in response to the stimulus.

8. The method of claim 7, wherein predicting when the plurality of events will occur comprises:

forecasting, in a plurality of time intervals, a plurality of invoiced amounts, respectively, of the plurality of medical claims; and forecasting, in the plurality of time intervals, a plurality of amounts of the payments, respectively, of the plurality of medical claims.

9. The method of claim 8, wherein the first information associated with the plurality of medical claims for services provided to the plurality of patients further comprises a plurality of identifiers for the plurality of payors, respectively, a plurality of billing codes for a plurality of encounters, respectively, and a plurality of dates at which the plurality of medical claims were submitted, respectively, to the plurality of payors, the method further comprising:

forecasting, in the plurality of time intervals, a plurality of amounts of the payments, respectively, of the plurality of medical claims for each of the plurality of identifiers of the plurality of payors based on the plurality of dates at which the plurality of medical claims were submitted, respectively, to the plurality of payors;

forecasting, in the plurality of time intervals, a plurality of amounts of the payments, respectively, of the medical claims for each of the plurality of billing codes for the plurality of encounters based on the plurality of dates at which the plurality of medical claims were submitted, respectively, to the plurality of payors;

determining, in the plurality of time intervals, a plurality of ideal amounts of the payments, respectively, of the plurality of medical claims for each of the plurality of identifiers of the plurality of payors based on the plurality of dates at which the plurality of medical claims were submitted, respectively, to the plurality of payors; and determining in the plurality of time intervals, a plurality of ideal amounts of the payments, respectively, of the medical claims for each of the plurality of billing codes for the plurality of encounters based on the plurality of dates at which the plurality of medical claims were submitted, respectively, to the plurality of payors.

10. A system, comprising:
a processor; and
a memory coupled to the processor and comprising computer readable program code embodied in the memory that is executable by the processor to perform operations comprising:
receiving information associated with a stimulus, the stimulus comprising a filing of a medical claim with a payor, the information associated with the stimulus comprising first information associated with a medical claim for services provided to a patient and second information associated with a provider that provided the services to the patient;
generating, using a machine learning engine, an artificial intelligence engine; and
predicting, using the artificial intelligence engine, when an event will occur in response to the stimulus, the event comprises payment of the medical claim by the payor;
wherein generating the artificial intelligence engine comprises:
receiving training information associated with the stimulus, the training information associated with the stimulus comprising first training information associated with a plurality of medical claims for services provided to a plurality of patients, respectively, the first training information comprising payment information associated with the plurality of medical claims, and second training information associated with a plurality of providers that provided the services to the plurality of patients;
detecting patterns in the training information associated with the stimulus;
training the machine learning engine based on the detected patterns detected in the training information associated with the stimulus; and
generating the artificial intelligence engine based on the machine learning engine that has been trained.

11. The system of claim 10, wherein the first information associated with the medical claim comprises an identifier for a payor, a billing code for an encounter, and/or a date at which the medical claim was submitted to the payor; and
wherein the second information associated with the provider comprises an identifier for the provider and/or a provider specialty.

12. A computer program product, comprising:
a non-transitory computer readable storage medium comprising computer readable program code embodied in the medium that is executable by a processor to perform operations comprising:
receiving information associated with a stimulus, the stimulus comprising a filing of a medical claim with a payor, the information associated with the stimulus comprising first information associated with a medical claim for services provided to a patient and second information associated with a provider that provided the services to the patient;
generating, using a machine learning engine, an artificial intelligence engine; and
predicting, using the artificial intelligence engine, when an event will occur in response to the stimulus, the event comprises payment of the medical claim by the payor;
wherein generating the artificial intelligence engine comprises:
receiving training information associated with the stimulus, the training information associated with the stimulus comprising first training information associated with a plurality of medical claims for services provided to a plurality of patients, respectively, the first training information comprising payment information associated with the plurality of medical claims, and second training information associated with a plurality of providers that provided the services to the plurality of patients;
detecting patterns in the training information associated with the stimulus;
training the machine learning engine based on the detected patterns detected in the training information associated with the stimulus; and
generating the artificial intelligence engine based on the machine learning engine that has been trained.

13. The computer program product of claim 12, wherein the first information associated with the medical claim comprises an identifier for a payor, a billing code for an encounter, and/or a date at which the medical claim was submitted to the payor; and
wherein the second information associated with the provider comprises an identifier for the provider and/or a provider specialty.

* * * * *